(12) United States Patent
Ki et al.

(10) Patent No.: US 12,161,665 B2
(45) Date of Patent: *Dec. 10, 2024

(54) CERIUM OXIDE NANOCOMPLEX AND A COMPOSITION FOR PREVENTING OR TREATING LIVER FAILURE COMPRISING THE SAME

(71) Applicant: Cenyx Biotech Inc., Seoul (KR)

(72) Inventors: Seul Ki Ki, Gongju-si (KR); So Hyun Jeon, Seoul (KR)

(73) Assignee: Cenyx Biotech Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/950,612

(22) Filed: Sep. 22, 2022

(65) Prior Publication Data

US 2023/0105614 A1    Apr. 6, 2023

Related U.S. Application Data

(60) Provisional application No. 63/247,520, filed on Sep. 23, 2021.

(51) Int. Cl.
*A61K 33/244* (2019.01)
*A61K 9/51* (2006.01)
*A61P 39/06* (2006.01)
*B82Y 5/00* (2011.01)

(52) U.S. Cl.
CPC .......... *A61K 33/244* (2019.01); *A61K 9/5138* (2013.01); *A61P 39/06* (2018.01); *B82Y 5/00* (2013.01)

(58) Field of Classification Search
CPC ..... A61P 39/06; A61K 33/244; A61K 9/5138; B82Y 5/00
See application file for complete search history.

(56) References Cited

U.S. PATENT DOCUMENTS

| 8,333,993 | B1 | 12/2012 | Perez et al. |
| 2010/0015188 | A1 | 1/2010 | Izu et al. |
| 2018/0078510 | A1 | 3/2018 | Alonso Fernandez et al. |
| 2019/0381187 | A1 | 12/2019 | Lee et al. |
| 2023/0114380 | A1* | 4/2023 | Lee ................... A61K 9/5146 424/497 |

FOREIGN PATENT DOCUMENTS

| KR | 10-2018-0043989 A | 5/2018 | |
| WO | WO-2020043668 A1 * | 3/2020 | ............. A61K 31/00 |

OTHER PUBLICATIONS

Oro' et al. (cerium oxide nanoparticles reduce steatosis, portal hypertension and display anti-inflammatory properties in rats with liver fibrosis), Journal of Hepatology, 2016 vol. 64, 691-698.*
Han-Gil Jeong, et al., "Ceria Nanoparticles Synthesized With Aminocaproic Acid for the Treatment of Subarachnoid Hemorrhage", Stroke, Dec. 2018, vol. 49, pp. 3030-3038 (9 pages total).
Gerardo Pulido-Reyes, et al., "Internalization and toxicological mechanisms of uncoated and PVP-coated cerium oxide nanoparticles in the freshwater alga *Chlamydomonas reinhardtii*", Environmental Science Nano, 2019, vol. 6, pp. 1959-1972 (14 pages total).
Yue Chen, et al., "The effects of PVP surfactant in the direct and indirect hydrothermal synthesis processes of ceria nanostructures", Ceramics International, 2016, vol. 42, pp. 18516-18520 (5 pages total).
International Search Report dated Jun. 25, 2021 issued in International Application No. PCT/KR2021/003737.
Office Action issued Oct. 13, 2023 in U.S. Appl. No. 17/950,638.
Communication dated Aug. 20, 2024, issued in U.S. Appl. No. 17/950,499.

* cited by examiner

*Primary Examiner* — Zohreh A Fay
(74) *Attorney, Agent, or Firm* — Sughrue Mion, PLLC (57) ABSTRACT

A cerium oxide nanocomplex, a composition containing the cerium oxide nanocomplex as an active ingredient, and their uses for preventing or treating inflammatory liver disease are disclosed. The present disclosure applies a biocompatible polymer composed of an optimal combination to significantly improve the biomedical stability, biosynthesis and efficiency of the production process of nanoparticles while maintaining the nanoparticles' excellent inhibitory activity against inflammation. In particular, the present disclosure may be applied as an effective therapeutic composition that effectively controls excessive immune response and inflammatory response and tissue injury in acute liver failure which is a serious condition of rapid loss of liver function that results in multiple organ failure and death.

7 Claims, 7 Drawing Sheets

100% aqueous solvent　　　　70% ethyl alcohol solvent

CERIUM OXIDE NANOCOMPLEX AND A COMPOSITION FOR PREVENTING OR TREATING LIVER FAILURE COMPRISING THE SAME

CROSS REFERENCE TO RELATED APPLICATIONS

This application claims benefit based on U.S. provisional application No. 63/247,520 filed Sep. 23, 2021, of which the entire content is incorporated by reference herein.

TECHNICAL FIELD

The present disclosure relates to a cerium oxide nanocomplex coated with a biocompatible dispersion stabilizer and a composition for preventing or treating liver failure, containing cerium oxide nanocomplex as an active ingredient.

BACKGROUND ART

Nanoparticles, which have been applied for various purposes in the field of diagnosis and treatment, exhibit new physical/chemical properties different from bulk materials in vivo due to their nanoscale size. Currently, many studies on the nanoparticles have been conducted and in this regard, vigorous efforts have been made to develop nanoparticles that exhibit optimal properties suitable for medical use by adjusting the particles' composition, shape, size, and properties, etc. as appropriate to the purpose.

Cerium oxide has thermal stability at high temperature and has a redox reaction of $Ce^{4+}/Ce^{3+}$ depending on the surrounding oxygen concentration due to its lattice structure, and thus has had various applications such as electrolytes of solid batteries, compositions for UV filters, oxygen sensors, optical devices, etc. Especially in the medical field, cerium oxide has been spotlighted as a therapeutic composition for a wide range of diseases caused by oxidative stress and inflammation due to its excellent ability to scavenge reactive oxygen species.

With a common method for the synthesis of cerium oxide nanoparticles, it is not only difficult to uniformly distribute the particles in a nanoscale, but also it is not easy to synthesize the particles in a fine size of 10 nm or less. For example, cerium oxide nanoparticles synthesized through a hydrothermal method, which is one of the aqueous phase-based methods, usually have a size ranging from several hundred nm to several microns, and because of this, it is difficult to precisely control the particle size and the particles show poor dispersibility. Therefore, methods for preparing cerium oxide nanoparticles having a smaller average particle size and a uniform size distribution have been proposed, but these methods are not suitable for industrial bulk production because they require an inefficient process involving a high-temperature processing at hundreds of ° C.

Accordingly, there is a need to develop a new method that may efficiently produce cerium oxide nanoparticles that have a size of 50 nm or less, uniform size distribution and good dispersibility, are facile to produce and maintain a unique antioxidant effect in a moderate reaction condition.

Meanwhile, acute liver failure is loss of liver function that occurs in a person with no previous liver disease. It is a serious condition that can be life-threatening. Acute liver failure can progress into hepatic encephalopathy within 2-8 weeks from the onset of first symptom. Acute liver failure is usually found among healthy people in their 30s and may induce liver dysfunction, increased level of liver enzymes, coagulopathy, and encephalopathy. The disease requires special attention in treatment as half of the patients suffer multiple organ failure and even death. The causes of acute liver failure are virus infection (Hepatitis A, hepatitis B, hepatitis E, herpes simplex virus, cytomegalovirus, Epstein-Barr virus, parvovirus, etc.), drug-induced hepatotoxicity (acetaminophen), alcohol, ischemic hepatitis, neoplastic infiltration, acute Budd-Chiari syndrome, heatstroke, mushroom poisoning, metabolic disease (Wilson's disease), etc. and despite various efforts, it is difficult to diagnose the causes in some cases.

Acute liver failure occurs following the primary injury resulting from any cause. Then pathogen-specific molecular patterns (PAMPs), damaged-associated molecular patterns (DAMP) from the damaged liver cells activate innate immune response and the secondary injury begins. The innate immune response involves various cell types including monocytes, macrophages, dendritic cells, leukocytes, and natural killer cells.

The treatment of acute liver failure aims to address metabolic and hemodynamic instability by using conservative treatment such as provision of appropriate nutrition and nutrient solution, prevention of infection and brain edema along with to treat specific cause of the disease. Liver transplantation may help restore liver function, but only 25% of patients with acute liver failure receive liver transplantation, and the fundamental treatment to effectively inhibit innate immune response which is the most critical in terms of pathophysiological aspect has not yet been developed, which calls for the development of a new anti-inflammatory therapeutic composition for effective inhibition.

A number of papers and patent documents are referenced throughout the present specification and citations thereof are shown. The disclosure of the cited papers and patent documents is incorporated herein by reference in their entirety to more clearly describe the level of the technical field to which the present disclosure pertains and the content of the present disclosure.

DISCLOSURE

Technical Problem

The present inventors have made intensive efforts to develop a nanoparticle-based therapeutic composition that can effectively inhibit innate immune response activation and initial inflammatory response in liver disease which is loss of normal physiological function in liver resulting from excessive immune and inflammatory responses due to various causes. As a result, the present disclosure has been completed by finding that when a polymer in which a monomer of a pyrrolidone derivative of Formula 1 is repeated is formed on the core of the cerium oxide nanoparticles, the present nanoparticles may be used as excellent therapeutic composition that not only significantly reduces the reactive oxygen species in vivo but also effectively inhibits inflammatory irritation and minimizes hepatotoxicity and tissue injury.

Thus, an object of the present disclosure is to provide a therapeutic composition for preventing or treating inflammatory liver disease, containing a cerium oxide nanocomplex.

Other objects and advantages of the present disclosure will be made clearer by the following detailed description of the disclosures, claims and drawings.

Technical Solution

In an aspect, there is provided a composition for preventing or treating inflammatory liver disease, comprising a cerium oxide nanocomplex as an active ingredient comprising:
(a) core layer of cerium oxide nanoparticles; and
(b) an inner layer including a polymer represented by the following Formula 1.

Formula 1 wherein $R_1$ and $R_2$ ⋰⋰⋰ are each independently hydrogen or oxygen, represents a single bond or a double bond, I is 1 or 2, and m is an integer of 100 to 1000.

The present inventors have made intensive efforts to develop a nanoparticle-based therapeutic composition that can effectively inhibit innate immune response activation and initial inflammatory response in liver disease which is loss of normal physiological function in liver resulting from excessive immune and inflammatory response due to various causes. As a result, the present inventors have found that when a polymer in which a monomer of a pyrrolidone derivative of Formula 1 is repeated is formed on the core of the cerium oxide nanoparticles, the present nanoparticles may be used as an excellent therapeutic composition that not only significantly reduces reactive oxygen species in vivo but also effectively inhibits inflammatory irritation and minimizes hepatotoxicity and tissue injury.

In particular, as seen from the examples described later in Examples section, the nanocomplex of the present disclosure can stably and economically bulk-produce uniform and fine particles for a sufficient reaction time without a harsh environment such as a strong base and strong acid condition at a high temperature. The related art requires a strong acid/strong base such as HCl and NaOH at a high temperature of 95° C. for an extremely short reaction time within 1 minute because polyethylene glycol (PEG) or a PEG derivative modified with a succinimidyl group is mainly used in order to ensure stability in vivo in the synthesis process of the cerium oxide nanoparticles, and thus has suffered great difficulties in obtaining a large amount of uniform particles. However, the nanocomplex according to the present disclosure secures stable synthesis conditions such as a reaction time of about 2 hours at 70° C., but also does not require a strong acid or strong base environment, and thus, has effectively overcome the disadvantages of the related art.

As used herein, the term "core layer" refers to an innermost layer having only one surface in contact with other layers in a multilayer composite.

As used herein, the term "multilayer composite" refers to a composite consisting of a plurality of layers composed of different components, and includes, without limitation, a laminated multilayer structure, a core-shell multilayer structure, and combinations thereof. Specifically, the multilayer composite according to the present disclosure has a core-shell type multilayer structure in which nanoparticles are present at the center and the polymer of Formula 1 and a biocompatible dispersion stabilizer surround the nanoparticles on the outer shell.

The process where a polymer represented by Formula 1 is formed by surrounding the core of the cerium oxide nanoparticle can be achieved by coating the polymer represented by Formula 1 on the surface of core layer.

As used herein, the term "coating" refers to forming a new layer having a certain thickness by applying a specific material on a target surface, and the target surface and the coating material may be coated through ionic or non-covalent bond. The term "non-covalent bond is a concept that includes not only physical bonds such as adsorption, cohesion, entanglement, and entrapment, but also bonds in which the interaction such as hydrogen bonds and van der Waals bonds occurs alone or in combination with the physical bonds described above. When coated with the polymer of formula 1, a closed layer may be formed while completely surrounding the surface to be modified, or may form a partially closed layer.

As used herein, the term "polymer" refers to a synthetic or natural polymer compound in which the same or different types of monomers are continuously linked. Thus, the polymer includes a homopolymer (a polymer in which one type of monomer is polymerized) and an interpolymer prepared by the polymerization of at least two different monomers, wherein the interpolymer includes both a copolymer (a polymer prepared from two different monomers) and a polymer prepared from more than two different monomers. Specifically, the polymer of Formula 1 used in the present disclosure is a homopolymer.

As used herein, the term "alkyl" refers to a straight or branched chain, saturated hydrocarbon group, and includes, for examples, methyl, ethyl, propyl, isopropyl, etc. $C_1$-$C_3$ alkyl refers to an alkyl group having an alkyl unit having 1 to 3 carbon atoms, and when $C_1$-$C_3$ alkyl is substituted, the number of carbon atoms in the substituent is not included.

As used herein, the term "biocompatibility" refers to a property of not causing short-term or long-term side effects when administered in vivo and in contact with cells, tissues or body fluids of organs, and specifically, refers to not only tissue compatibility and blood compatibility that do not cause tissue necrosis or blood coagulation in contact with biological tissue or blood, but also biodegradability, which is a property of being disappeared after a certain period of time after in vivo administration of the material, and "excretability, which is a property of being excreted outside the body without accumulation after in vivo administration of the material." Thus, the term "biocompatible dispersion stabilizer" refers to a component that improves the dispersibility of particles while having the biocompatibility described above.

As used herein, the term "biodegradability" refers to a property of the material to naturally decompose when exposed to a physiological solution having a pH of 6 to 8, and specifically, refers to a property in which the material may be decomposed over time by body fluids, decomposing enzymes, or microorganisms, etc., in vivo.

According to a specific embodiment of the present disclosure, the cerium oxide nanoparticles used in the present disclosure may be cerium(IV) oxide ($CeO_2$), cerium(III) oxide ($Ce_2O_3$), or a mixture thereof.

According to a specific embodiment of the present disclosure, in Formula 1, $R^1$ is hydrogen, $R_2$ is oxygen, and I is 1. According to an octet rule, it is obvious that when $R^1$ is hydrogen, ≈≈≈ is a single bond, and when $R_2$ is oxygen, ≈≈≈ is a double bond. The compound of Formula 1 wherein $R_1$ is hydrogen, $R_2$ is oxygen, and I is 1 is polyvinylpyrrolidone (PVP).

According to a specific embodiment of the present disclosure, the nanocomplex of the present disclosure further comprises an outer layer that comprises one or more biocompatible dispersion stabilizers selected from the group consisting of polyglutamic acid (PGA), poly(aspartic acid) (PASP), alginate, poly(acrylic acid) (PAA), poly(methacrylic acid) (PMAA), poly(methyl methacrylic acid), poly(maleic acid) (PMA), poly(butadiene/maleic acid) (PBMA), poly(vinylphosphonic acid) (PVPA), poly(styrenesulfonic acid) (PSSA), polyvinyl alcohol (PVA) and dextran.

As used herein, the term "inner layer" refers to a layer closer to the core than the outer layer, and the term "outer layer" refers to a layer that surrounds the inner layer of a core-shell structure and is further away from the core than the inner layer. The inner layer does not necessarily have to be a layer in direct contact with the core layer and an additional layer closer to the core layer than the inner layer may be present. The outer layer also does not necessarily have to be an outermost layer, and the outermost layer located farther away from the core than the outer layer may be further present.

According to the present disclosure, the boundary between the core layer and the inner layer is clearly distinguished, but the boundary between the inner layer and the outer layer may or may not be clearly distinguished. If a boundary between the inner layer and the outer layer is not clear, each component of the inner layer and the outer layer may be mixed in the vicinity of the interface or in the entire section.

According to a specific embodiment of the present disclosure, the biocompatible dispersion stabilizer included in the outer layer is polyglutamic acid (PGA). Polyglutamic acid (PGA) may be poly-α-glutamic acid, poly-β-glutamic acid, or poly-γ-glutamic acid, specifically poly-α-glutamic acid. Most specifically, the poly-α-glutamic acid is poly(L-glutamic acid) (PLGA).

According to a specific embodiment of the present disclosure, the nanocomplex according to the present disclosure further includes a multifunctional ligand represented by the following Formula 2:

Formula 2 wherein n is an integer of 3 to 7.

As used herein, the term "multi-functional ligand" refers to a molecule having two or more active functional groups and binding to two or more molecules, thereby serving as a linker between the molecules. The multi-functional ligand of Formula 2 used in the present disclosure has a carboxyl group capable of binding to cerium oxide nanoparticles and an amine group capable of binding to PVP in the inner layer and/or PGA, PVA or dextran in the outer layer to enable the nanocomplex according to the present disclosure to be formed more efficiently and stably.

Specifically, in the above Formula 2, n is 5. The compound of Formula 2 wherein n is 5 is 6-aminohexanoic acid (6-AHA).

According to a specific embodiment of the present disclosure, the nanocomplex according to the present disclosure has an average particle size of 5 nm to 100 nm. The nanocomplex has an average particle size of more specifically 5 nm to 80 nm, and most specifically 5 nm to 50 nm.

As used herein, the term "inflammatory liver disease" refers to a group of diseases that involve liver tissue damage or function loss which is directly or indirectly caused by excessive or unwanted immune response or inflammatory response arising from various causes.

According to a specific embodiment of the present disclosure, the inflammatory liver disease that may be prevented or treated by the present disclosure is selected from a group consisting of viral hepatitis, *toxoplasma* hepatitis, alcoholic liver disease, toxic liver disease, liver failure, liver abscess, nonspecific reactive hepatitis, liver infarction, hepatic veno-occlusive disease, injury of liver or gallbladder and liver transplantation-related hepatitis.

More specifically, the above inflammatory liver disease is liver failure.

As used herein, the term "liver failure" refers to a pathological condition where a normal physiological actions including protein synthesis and/or metabolic action due to liver tissue injury may not be performed. In most cases, liver failure is not a minor functional decline but a serious disease that is life-threatening. As seen from the examples described later in Examples section, the composition of the present disclosure effectively protects liver tissue from inflammation-induced hepatotoxicity, and therefore has a therapeutic effect for both acute liver failure which occurs without any preexisting liver diseases and chronic liver failure which develops over a long time as the result of damage caused by long-term liver disease.

Acute liver failure is a rapid loss of liver function resulting from virus infection, adverse effect from drug/poison intake, ischemia, neoplastic infiltration, metabolic disease, etc. The disease can occur in a patient without preexisting liver disease or a patient who has liver disease but those whose condition does not progress into liver cirrhosis. Meanwhile, chronic liver failure is a pathologic condition of liver tissue that occurs at the final stage of chronic preexisting conditions such as alcoholic liver disease, chronic viral hepatitis, primary sclerosing cholangitis, etc. Symptoms do not appear in the early stages of the disease, however, the liver function gradually deteriorates.

More specifically, the liver failure that may be prevented or treated with the composition of the present disclosure is acute or subacute liver failure.

Acute liver failure occurs as hepatic cells are damaged by various causes, and the damaged cells initiate innate immune response and activate immune cells including monocytes, macrophages, dendritic cells, leukocytes, natural killer cells, etc. Therefore, along with removing the causes of primary injury, effective inhibition of innate immune response following the primary injury is very important in pathophysiological aspect of the treatment of acute liver failure.

As used herein, the term "prevention" refers to inhibiting the development of a disease or condition in a subject who has not been diagnosed with the disease or condition, but is likely to be afflicted with such a disease or illness.

As used herein, the term "treatment" refers to (a) inhibiting the progression of the disease, illness, or symptom; (b) alleviating the disease, illness, or symptom; or (c) eliminating the disease, illness, or symptom. The composition of the present disclosure reduces reactive oxygen species to inhibit or eliminate or alleviate inflammatory response, especially the excessive activation of innate immune response in hepatic tissue and the progress and development of inflammation.

Thus, the composition according to the present disclosure may itself be a composition for treating these diseases, or may be administered in conjunction with other pharmacological ingredients having an anti-inflammatory effect and applied as a therapeutic adjuvant for the above diseases. Accordingly, as used herein, the term "treatment" or "therapeutic agent" includes the meaning of "therapeutic aid" or a "therapeutic adjuvant."

As used herein, the term "administration" refers to administration of a therapeutically effective amount of the composition according to the present disclosure directly to a subject so that the same amount is formed in the body of the subject, and has the same meaning as "transplantation" or "injection."

As used herein, the term "therapeutically effective amount" refers to the amount of the composition contained in an amount sufficient to provide a therapeutic or prophylactic effect to an individual who wishes to administer the composition according to the present disclosure, and is therefore meant to include "prophylactically effective amount."

As used herein, the term "subject" includes, without limitation, human, mouse, rat, guinea pig, dog, cat, horse, cow, pig, monkey, chimpanzee, baboon, or rhesus monkey. Specifically, the subject is a human.

When the composition according to the present disclosure is prepared as a pharmaceutical composition, the pharmaceutical composition according to the present disclosure contains a pharmaceutically acceptable carrier. Pharmaceutically acceptable carriers contained in the pharmaceutical composition according to the present disclosure are commonly used in preparation, and examples thereof include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, etc. The pharmaceutical composition according to the present disclosure may further contain lubricants, wetting agents, sweetening agents, flavoring agents, emulsifying agents, suspending agents, preservatives, etc., in addition to the above components. Suitable pharmaceutically acceptable carriers and formulations are described in detail in Remington's Pharmaceutical Sciences (19th ed., 1995).

The pharmaceutical composition according to the present disclosure may be administered through various routes of administration, specifically, parenterally, and more specifically, orally, intravenously, intraarterially, subcutaneously, intraperitoneally, intradermally, intramuscularly, intraventricularly, intrathecally, inhalationally, nasally, intraarticularly, or topically.

A suitable dosage of the pharmaceutical composition according to the present disclosure may be variously prescribed depending on factors such as formulation method, administration mode, age, weight, sex, pathological condition, food, administration time, administration route, excretion rate, and response sensitivity of the patient. A preferred dosage of the pharmaceutical composition according to the present disclosure is within the range of 0.0001 to 100 mg/kg for adults.

The pharmaceutical composition according to the present disclosure may be prepared in unit dosage form by formulating with a pharmaceutically acceptable carrier and/or excipient, or may be prepared by introduction into a multi-dose container, according to a method that may be easily carried out by a person of ordinary skill in the art to which the present disclosure pertains. In this case, the preparation may be in the form of solutions, suspensions, syrups, or emulsions in oil or aqueous medium, or may also be in the form of extracts, powders, granules, tablets or capsules, and may additionally include dispersants or stabilizers.

Advantageous Effects

The features and advantages of the present disclosure are summarized as follows:
 (a) the present disclosure provides a cerium oxide nanocomplex, a method for preparing the same, and a composition for preventing or treating brain edema, containing the cerium oxide nanocomplex as an active ingredient, and
 (b) the present disclosure may be usefully used as an efficient nanoparticle therapeutic composition by applying a biocompatible polymer composed of an optimal combination to significantly improve the biomedical stability, biocompatibility, and efficiency of the production process of nanoparticles while maintaining excellent inhibitory activity against by applying a biocompatible polymer composed of an optimal combination.
 (c) The present disclosure, in particular, may be usefully used as an excellent therapeutic composition that may effectively inhibit excessive immune response and inflammatory response, and quickly block tissue damage in acute liver failure, that is a serious disease resulting in multiple organ failure and death due to sudden and rapid loss of liver function.

BRIEF DESCRIPTION OF THE DRAWINGS

FIG. 9a, FIG. 9b, and FIG. 9c show the results of measuring ALT (FIG. 9a), AST (FIG. 9b), and liver tissue weight (FIG. 9c) in Sprague-Dawley (SD) rats. The rats were first injected with D-Galactosamine (GaIN) Hydrochlroride and LPS to induce inflammatory irritation. Then nanocomplex of the present disclosure was administered and the corresponding changes in ALT, AST and liver tissue weight were measured. G1, normal rats; G2, positive control group, G3, a group injected with 0.1 mg/kg of cerium oxide nanocomplex, G4, a group injected with 0.5 mg/kg of cerium oxide nanocomplex.

BEST MODE

Hereinafter, the present disclosure will be described in detail with reference to the following examples. These examples are only for illustrating the present disclosure in more detail, and it will be apparent to those of ordinary skill in the art that the scope of the present disclosure.

EXAMPLES

Examples 1: Synthesis of Cerium Oxide Nanocomplex

Figure 1:
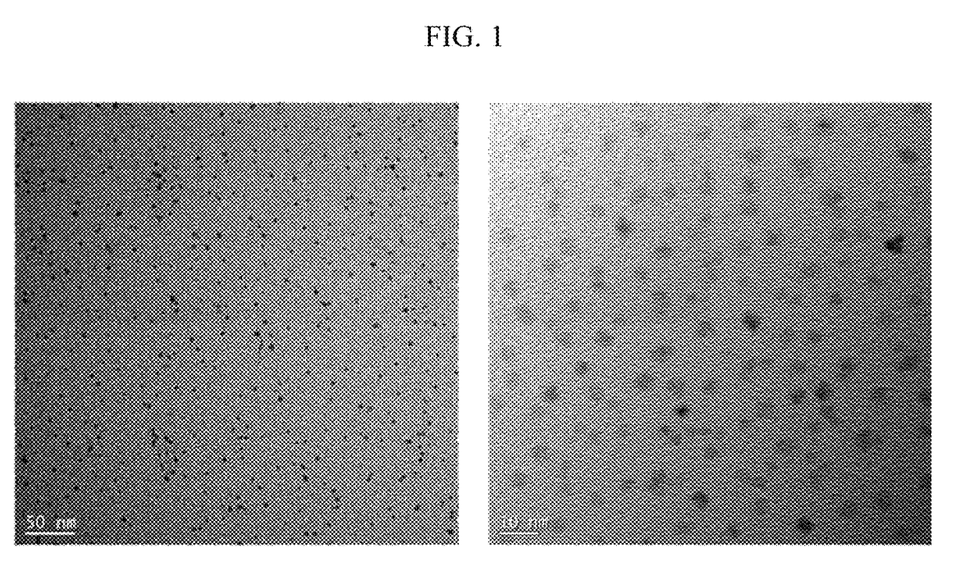
FIG. 1 is a diagram illustrating a transmission electron microscope image of a cerium oxide nanocomplex according to the present disclosure.

A first solution was prepared by dissolving 6-aminohexanoic acid (6-AHA) (0.65585 g, Sigma-Aldrich, St. Louis, MO) in deionized water (30 mL). A third solution was prepared by adding a second solution in which polyvinylpyrrolidone (PVP) (2.0 g, Sigma-Aldrich, St. Louis, MO) was dissolved in ethyl alcohol (25 mL) and heating the second solution to 70° C. in air while stirring the first solution. Meanwhile, a fourth solution was prepared by dissolving cerium(III) nitrate hexahydrate ($Ce(NO_3)_3 \cdot 6H_2O$, 0.540 g, Alfa Aeser, Ward Hill, MA) in ethyl alcohol (50 mL) at room temperature (about 20° C.). Thereafter, a fifth solution was prepared by adding the fourth solution to the third solution. Then, the temperature of the fifth solution was maintained at 70° C. for 2 hours, and then cooled to room temperature (about 20° C.). Through such a process, cerium oxide nanoparticles in which 6-aminohexanoic acid and polyvinyl pyrrolidone were bound to the surface, were obtained (FIG. 1). Next, the cerium oxide nanoparticles were washed three times with acetone to remove unreacted materials.

Example 2: Synthesis Trend of Cerium Oxide Nanocomplex Depending on Solvent

In order to identify the formation tendency of particles depending on the synthetic solvent, the formation state of the cerium oxide nanocomplex was confirmed by using a 100% aqueous solvent or a 70% ethyl alcohol solvent.
100% Aqueous Solvent
A first solution was prepared by dissolving 6-aminohexanoic acid (0.65585 g, Sigma-Aldrich, St. Louis, MO) in deionized water (30 mL), and a third solution was prepared by adding a second solution in which polyvinylpyrrolidone (2.0 g, Sigma-Aldrich, St. Louis, MO) was dissolved in deionized water (25 mL) during stirring of the first solution, and then heating the second solution to 70° C. in air. Meanwhile, a fourth solution was prepared by dissolving cerium(III) nitrate hexahydrate ($Ce(NO_3)_3 \cdot 6H_2O$, 0.540 g, Alfa Aeser, Ward Hill, MA) in deionized water (50 mL) at room temperature (about 20° C.). Thereafter, a fifth solution was prepared by adding the fourth solution to the third solution. Then, the temperature of the fifth solution was maintained at 70° C. for 2 hours, and then cooled to room temperature (about 20° C.) to obtain cerium oxide nanoparticles in which 6-aminohexanoic acid and polyvinylpyrrolidone were bonded to the surface. Next, the cerium oxide nanoparticles were washed three times with acetone to remove unreacted materials.
70% Ethyl Alcohol Solvent:
The solvent was obtained in the same manner as in the Example 1.

Figure 2:
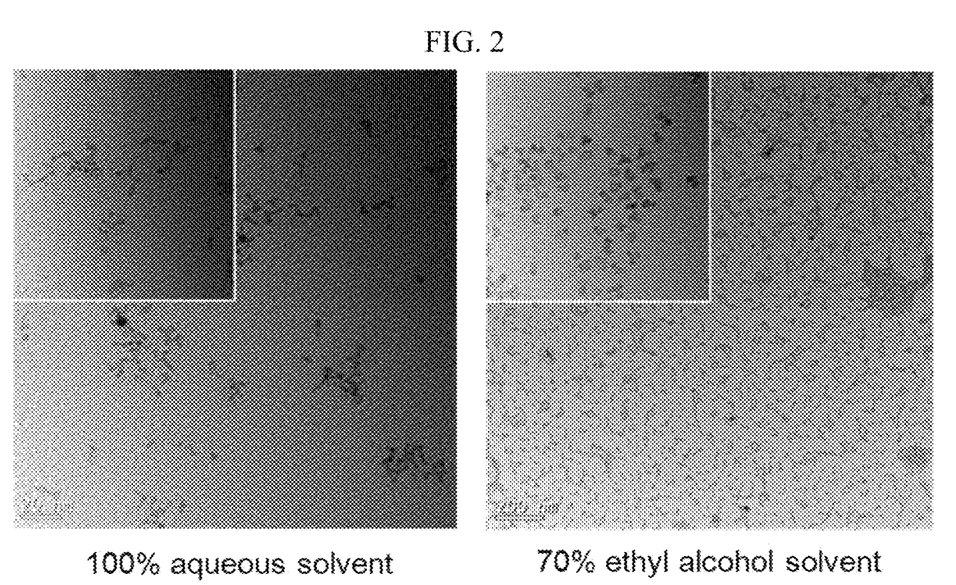
FIG. 2 is a diagram illustrating results of analyzing the shape and dispersion of the cerium oxide nanocomplex depending on the properties of the solvent.

As the result of analyzing the transmission electron microscopy image, it could be confirmed that the cerium oxide nanocomplex synthesized with 100% aqueous solvent was difficult to identify the individual dispersibility of the particles, and was entangled with each other and aggregated like a spider web, whereas the cerium oxide nanocomplex synthesized with 70% ethyl alcohol solvent had high dispersibility of particles (FIG. 2). It was found from the above results that the alcohol solvent is more advantageous than the aqueous solvent in terms of the reaction rate and stable dispersibility of the particles.

Example 3: Structure Formation of Cerium Oxide Nanocomplex Depending on Components of Synthesis Reactant In order to confirm a structural change of the nanocomplex depending on whether or not 6-aminohexanoic acid and polyvinyl pyrrolidone is present during a synthesis process, 6-AHA and PVP were sequentially excluded from the synthesis process of Example 1, and finally, the experiment was conducted in a form including all additives. The particle size was analyzed using dynamic light scattering device.

Figure 3:
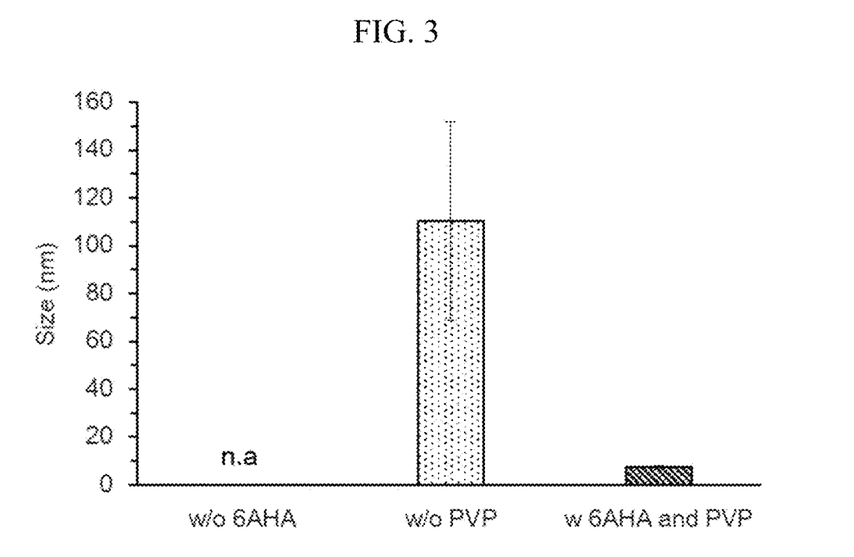
FIG. 3 is a diagram illustrating a particle size change of the cerium oxide nanocomplex depending on whether or not the compound is present.
Figure 4:
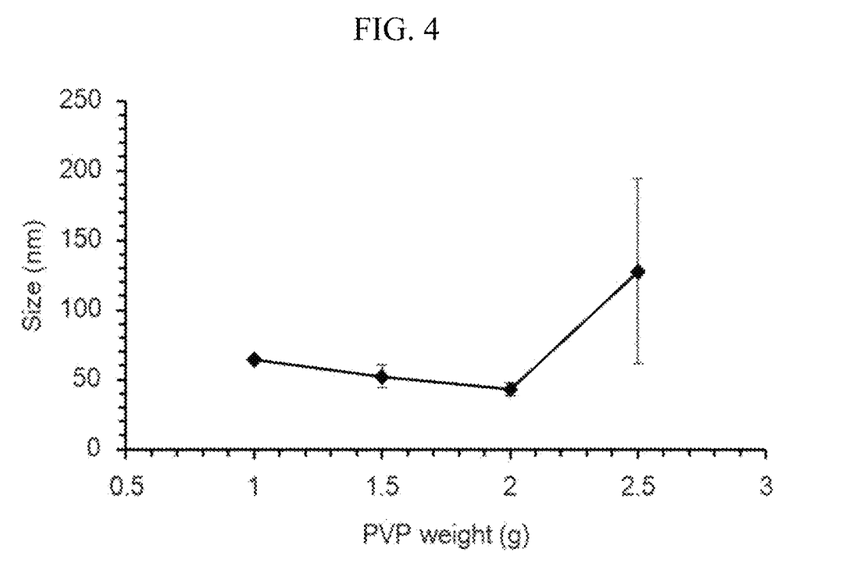
FIG. 4 is a diagram illustrating results of analyzing the particle size change depending on the amounts of polyvinyl pyrrolidone.

As a result, it was confirmed that no particles were formed in the absence of 6-AHA, and very large particles of 100 nm or more were formed in the absence of PVP, whereas uniform particles of 10 nm size were synthesized only when both 6-AHA and PVP were added to the synthesis (FIG. 3). Accordingly, it was confirmed that when two compounds, 6-AHA and PVP, were complementarily participated in the synthesis and were applied simultaneously, nanocomplex having a stable size and dispersity as a biomaterial may be efficiently obtained.

Example 4: Change in Formation of Nanocomplex Depending on Amounts of PVP

In order to confirm the tendency of nanocomplex formation depending on the amounts of PVP serving as a dispersion stabilizer in the present disclosure, the change in the nanocomplex formation was examined by using PVP of various amounts of 1.0, 1.5, 2.0 and 2.5 g in the synthesis process of Example 1. As a result of analyzing the synthesized particle size through dynamic light scattering analysis, it was possible to obtain uniform particles of the smallest size when PVP was used in a dose of 2.0 g (19 mg/ml). Considering the effect of the size of the nanocomplex on dispersity, function and biological stability, it can be said that this is the result of finding for the most suitable synthesis conditions.

Figure 5:
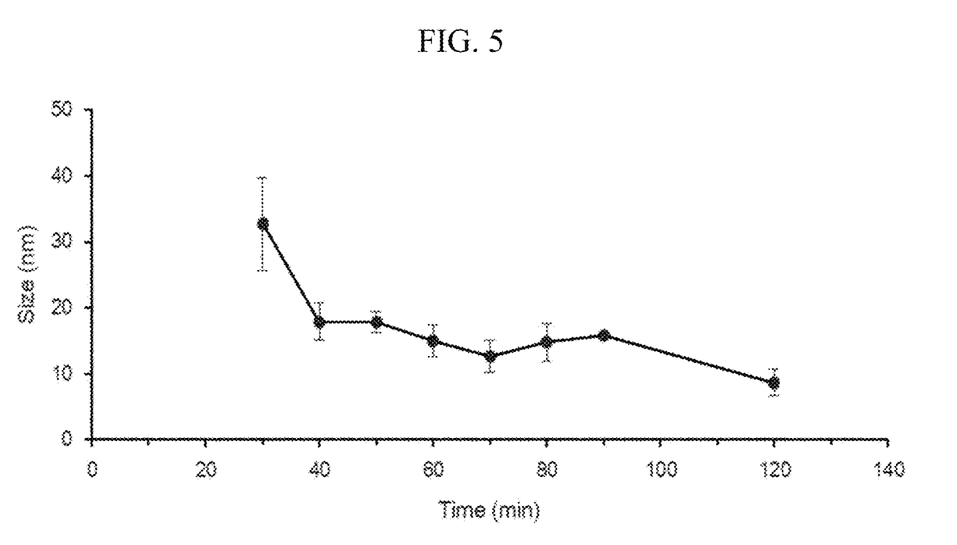
FIG. 5 is a diagram illustrating results of analyzing the particle size for each reaction time of the cerium oxide nanocomplex using a dynamic light scattering device.

Example 5: Size Formation Trend of Cerium Oxide Nanocomplex Depending on Synthesis Time In order to identify the particle size and stability of the cerium oxide nanocomplex that may be synthesized through Example 1 for each synthesis retention time, while the reaction of the fifth solution was maintained, samples were taken every 30, 40, 50, 60, 70, 80, 90, and 120 minutes, and the particle size was analyzed using dynamic light scattering device. As a result, it was confirmed that as the reaction time elapsed, the particle size gradually decreased from 30 nm to 5 nm, and each sample collected for each time had a very stable particle size. Therefore, it was confirmed that the method of the present disclosure is a process capable of manufacturing nanoparticles with remarkably excellent uniformity (FIG. 5).

Example 6: Coating of Cerium Oxide Nanocomplex with Biodispersion Stabilizer

A suspension was prepared by adding 3.5 mg of cerium oxide nanoparticles prepared through the above-mentioned process to 0.8 mL of sodium acetate buffer (2.5 mM). The suspension was mixed with 0.3 µmol of polyglutamic acid (PLGA) (weight average molecular weight: 9,000) or the same weight of polyvinyl alcohol (PVA) (weight average molecular weight: 9,500) and dextran (weight average molecular weight: 6,000) dissolved in 1.2 mL of sodium acetate buffer. The cerium oxide nanocomplex was obtained by stirring the mixture at room temperature for 5 minutes and combining positively charged 6-AHA bound to the surface of the cerium oxide nanoparticles and surface negatively charged the polyglutamic acid, polyvinyl alcohol, dextran, etc., by electrostatic attraction.

Figure 6A:
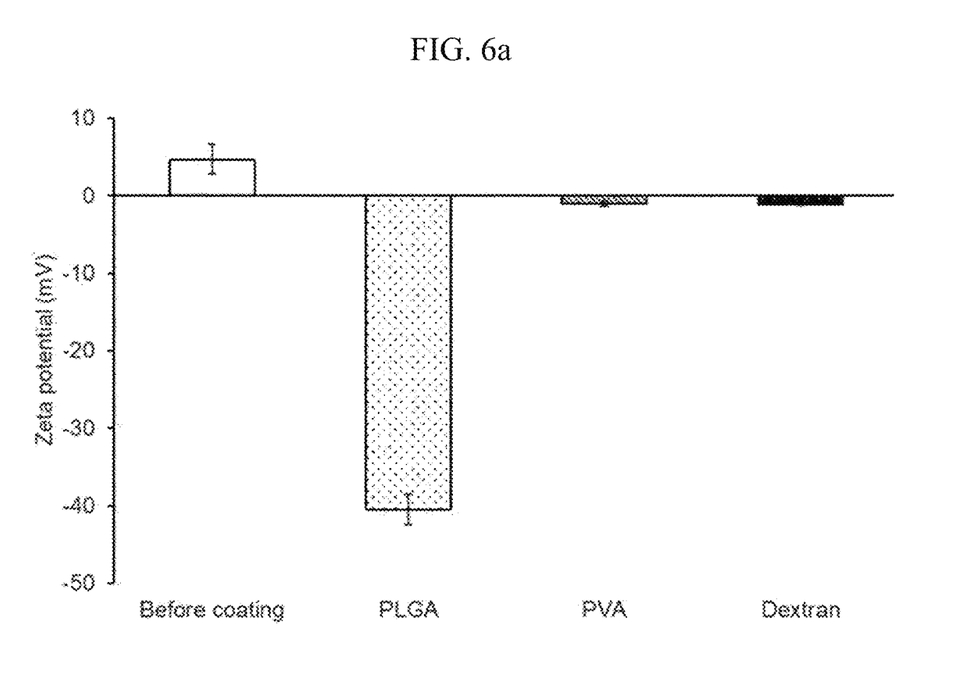
FIG. 6a is a diagram showing results of checking whether or not the cerium oxide nanocomplex are coated with a biocompatible dispersion stabilizer using a surface potential analysis device.

It was confirmed that the cerium oxide nanocomplex had a surface potential value of 5 mV before coating with a biocompatible dispersion stabilizer, and had a charge value of −40 mV after coating with PLGA, and a charge value close to −1 mV after coating with PVA and dextran, respectively. Also, it was confirmed that different biocompatible dispersion stabilizers were coated on the cerium oxide nanoparticles through this method (FIG. 6A).

Figure 6B:
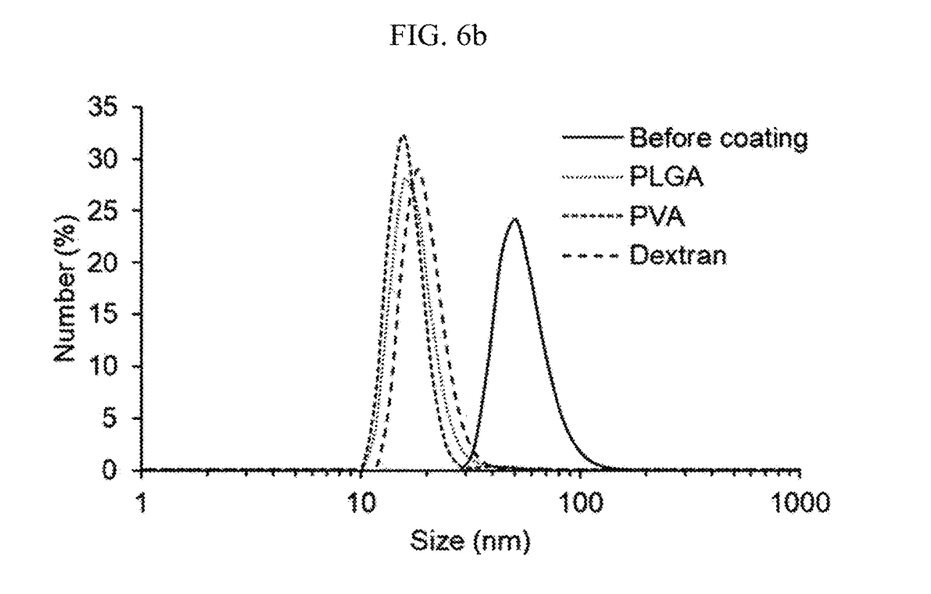
FIG. 6b illustrates results of analyzing the particle size of the cerium oxide nanocomplex using a dynamic light scattering device.

It was confirmed that in a dispersing environment of normal saline (an aqueous 0.9% (w/w) sodium chloride solution) that simulates the environment for use in actual biomedical applications, the cerium oxide nanocomplex had a size of 50 to 100 nm before coating with the biocompatible dispersion stabilizer, and the dispersion size was improved from 10 to 50 nm in all conditions using each dispersion stabilizer after coating with the biocompatible dispersion stabilizer (FIG. 6B).

Example 7: Evaluation of Antioxidant Effect of Cerium Oxide Nanocomplex

Figure 7A:
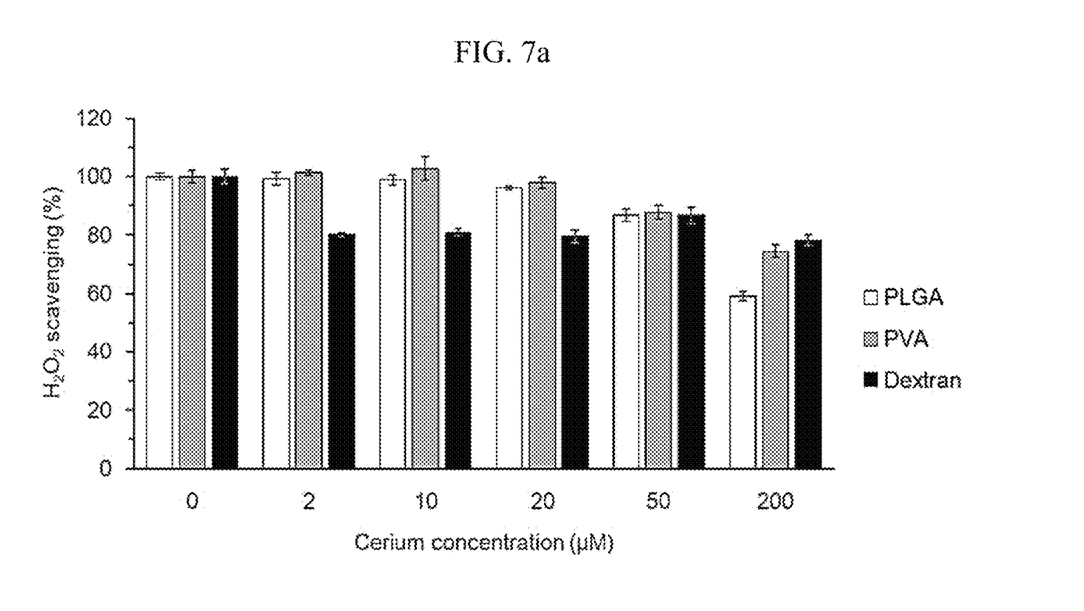
FIG. 7a and FIG. 7b are diagrams illustrating the evaluation results of hydrogen peroxide and hydroxyl radical scavenging capacity of the cerium oxide nanocomplex.
Figure 7B:
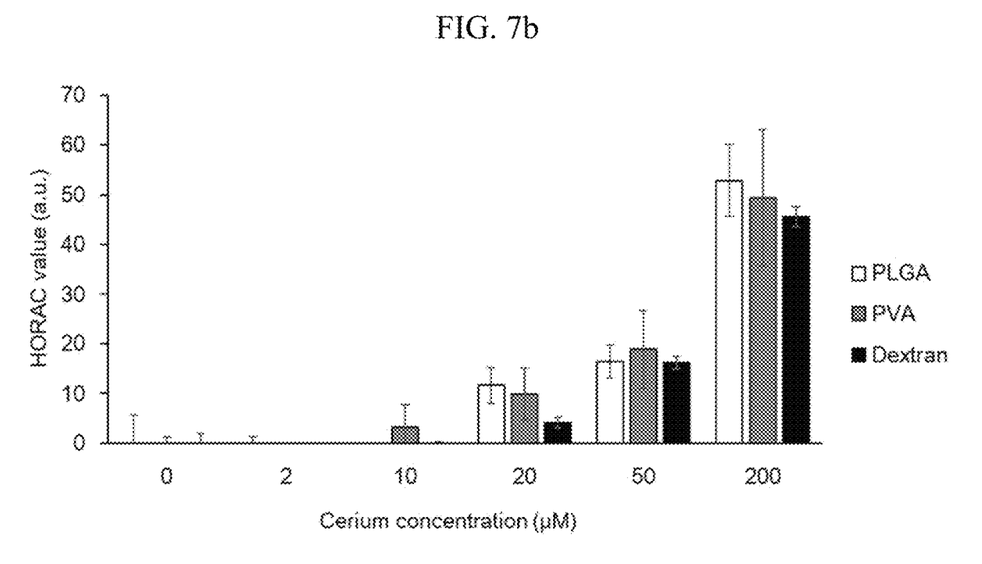

In order to determine the antioxidant effect of the cerium oxide nanocomplex coated with different biocompatible dispersion stabilizers, the scavenging of representative reactive oxygen species, hydrogen peroxide ($H_2O_2$) and hydroxyl radicals (—OH), was investigated. For the analysis of each reactive oxygen species, an Amplex™ Red Hydergen Peroxide/Peroxidase Assay Kit was used for hydrogen peroxide, and hydroxyl radical antioxidant capacity (HORAC) assay was used for hydroxyl radicals. It was confirmed through each analysis that the cerium oxide nanocomplex not only had the function of scavenging various types of reactive oxygen species, but also that this function was proportional to the concentration of the particles (FIG. 7). In addition, it could be confirmed that although the cerium oxide nanocomplex was coated with different kinds of dispersion stabilizers, the ability to scavenge reactive oxygen species was derived from the core particles by successfully scavenging reactive oxygen species.

Figure 8:
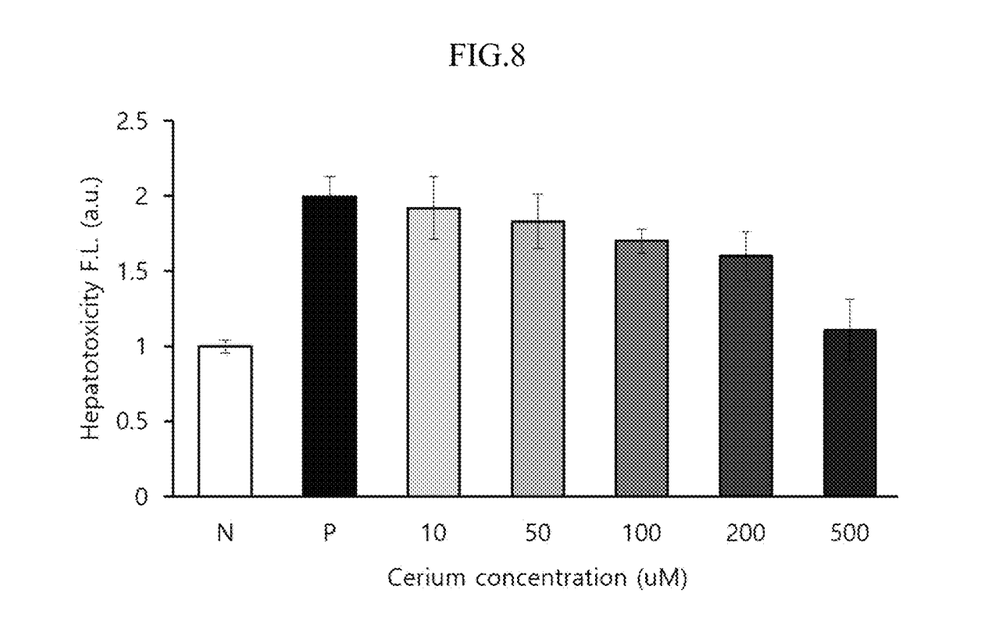
FIG. 8 is a graph showing results of evaluating the toxic stimulation associated with reactive oxygen species after treating hepatocytes (heap-1c1c7) in which the toxic stimulation is induced by pyrogallol with the nanocomplex of the present disclosure for each concentration.

Experimental Example 1: Treatment Effect of Cerium Oxide Nanocomplex for Infectious Inflammatory Disease—Inflammatory Liver Disease In order to investigate the therapeutic effect of cerium oxide nanocomplex for liver cell toxicity caused by inflammation, the degree of hepatotoxicity derived from pyrogallol was measured. In order to evaluate hepatotoxicity, hepatocytes (heap-1c1c7) were treated with pyrogallol to induce toxic stimuli, and the cerium oxide nanocomplex was treated for 1 hour at each concentration to evaluate the toxic stimulus associated with reactive oxygen species. As illustrated in FIG. 8, it was confirmed that the cerium oxide nanocomplex according to the present disclosure significantly reduced pyrogallol-induced hepatotoxicity in a concentration-dependent manner. It was confirmed that the cerium oxide nanocomplex had an excellent therapeutic effect on hepatocellular toxicity caused by inflammation by showing that hepatotoxicity in the group treated particularly with 500 µM of cerium oxide nanocomplex was reduced to a level similar to that of the negative control group.

Experimental Example 2: Treatment Effect of Cerium Oxide Nanocomplex for Acute Liver Failure Verified Through Inhibition of Liver Enzymes

Figure 9A:
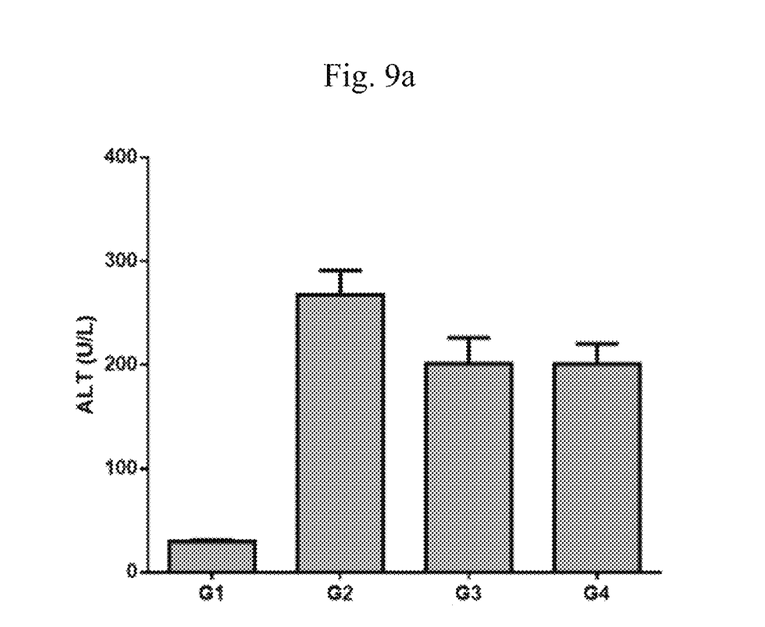
Figure 9B:
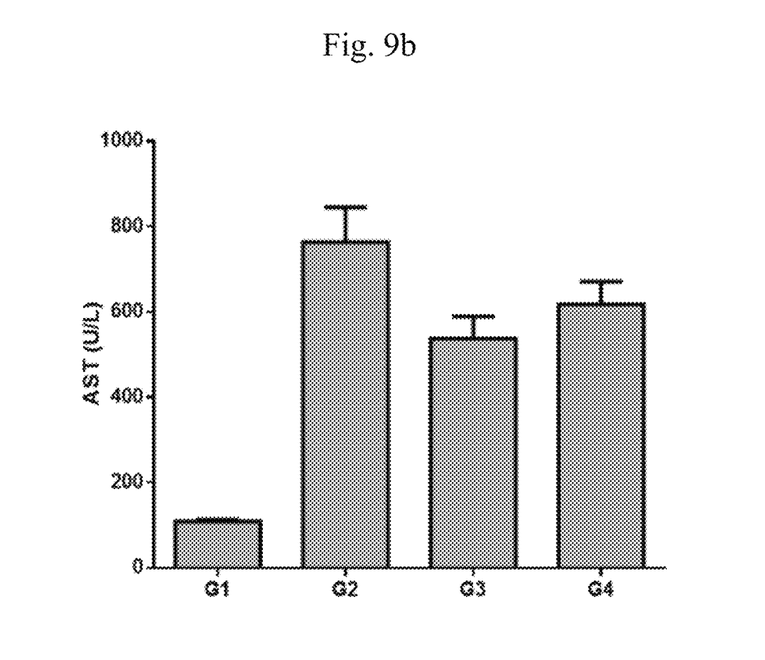
Figure 9C:
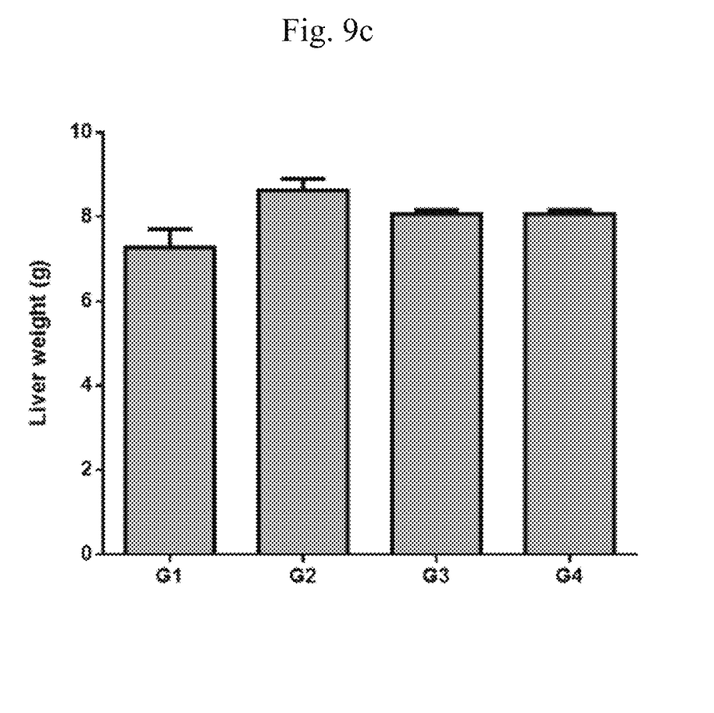

In order to confirm the therapeutic effect of the cerium oxide nanocomplex prepared in the present disclosure for acute liver failure, Sprague-Dawley (SD) rats were used to induce a model of acute liver failure. Specifically, 700 mg/kg of D-Galactosamine hydrochloride (GaIN) and 1 µg/kg of lipopolysaccharide (LPS) were injected into the abdominal cavity of SD rats once. After 130 minutes, 0.1 mg Ce/kg (G3, 12 rats) or 0.5 mg Ce/kg (G4, 12 rats) of the cerium oxide nanocomplex of the present disclosure was intravenously injected with a disposable syringe for around one minute, or the saline of the same volume was intravenously injected into the control group (G2, 12 rats). Also, six rats (G1) were set as a normal group into which any material including GaIN and LPS was not injected. At the 8th hour from the injection of GaIN and LPS, blood from all living animals was collected and put into SST tube which was centrifugated to separate serum. After blood collection was completed, a forensic autopsy was performed on hepatic tissue of all groups. The alanine aminotransferase (ALT) and aspartate aminotransferase (AST) of separate serum were measured using a blood physicochemical analyzer (7180, HITACHI, Japan). Also, the weight of harvested liver tissue was measured and recorded. As a result, it was confirmed that the ALT and AST significantly decreased in rats injected with the cerium oxide nanocomplex compared with those of control group. (FIGS. 9a and 9b). Also, it was confirmed that the weight of livers of rats injected with the cerium oxide nanocomplex was higher than those of control group.

Specific portions of the present disclosure have been described in detail hereinabove, but it is obvious to those skilled in the art that such a specific description is only an exemplary embodiment, and the scope of the present disclosure is not limited thereto. Therefore, the substantial scope of the present disclosure will be defined by the claims and equivalents thereof.

The invention claimed is:
1. A method for treating inflammatory liver disease, comprising administering to a subject in need thereof a cerium oxide nanocomplex comprising:

(a) a core layer of cerium oxide nanoparticles;
(b) an inner layer comprising a polymer of the following Formula 1 and a multifunctional ligand of the following Formula 2:

Formula 1 wherein $R_1$ is hydrogen, $R_2$ is oxygen, ⁓ represents a single bond or a double bond, l is 1, and m is an integer of 100 to 1000;

Formula 2 wherein n is 5; and (c) an outer layer comprising a polyglutamic acid (PGA).

2. The method of claim 1, wherein the cerium oxide nanoparticles are selected from the group consisting of cerium(III) oxide ($Ce_2O_3$) nanoparticles, cerium(IV) oxide ($CeO_2$) nanoparticles, and a mixture thereof.

3. The method of claim 1, wherein the PGA is poly L-glutamic acid (PLGA).

4. The method of claim 1, wherein the nanocomplex has an average particle size of 5 nm to 100 nm.

5. The method of claim 1, wherein the inflammatory liver disease is selected from the group consisting of viral hepatitis, toxoplasma hepatitis, alcoholic liver disease, toxic liver disease, liver failure, liver abscess, nonspecific reactive hepatitis, liver infarction, hepatic veno-occlusive disease, injury of liver, and liver transplantation-related hepatitis.

6. The method of claim 5, wherein the inflammatory liver disease is liver failure.

7. The method of claim 6, wherein the liver failure is acute or subacute liver failure.

* * * * *